Sept. 2, 1952 F. G. READ Plant Pat. 1,125
SHASTA DAISY PLANT
Filed June 20, 1951
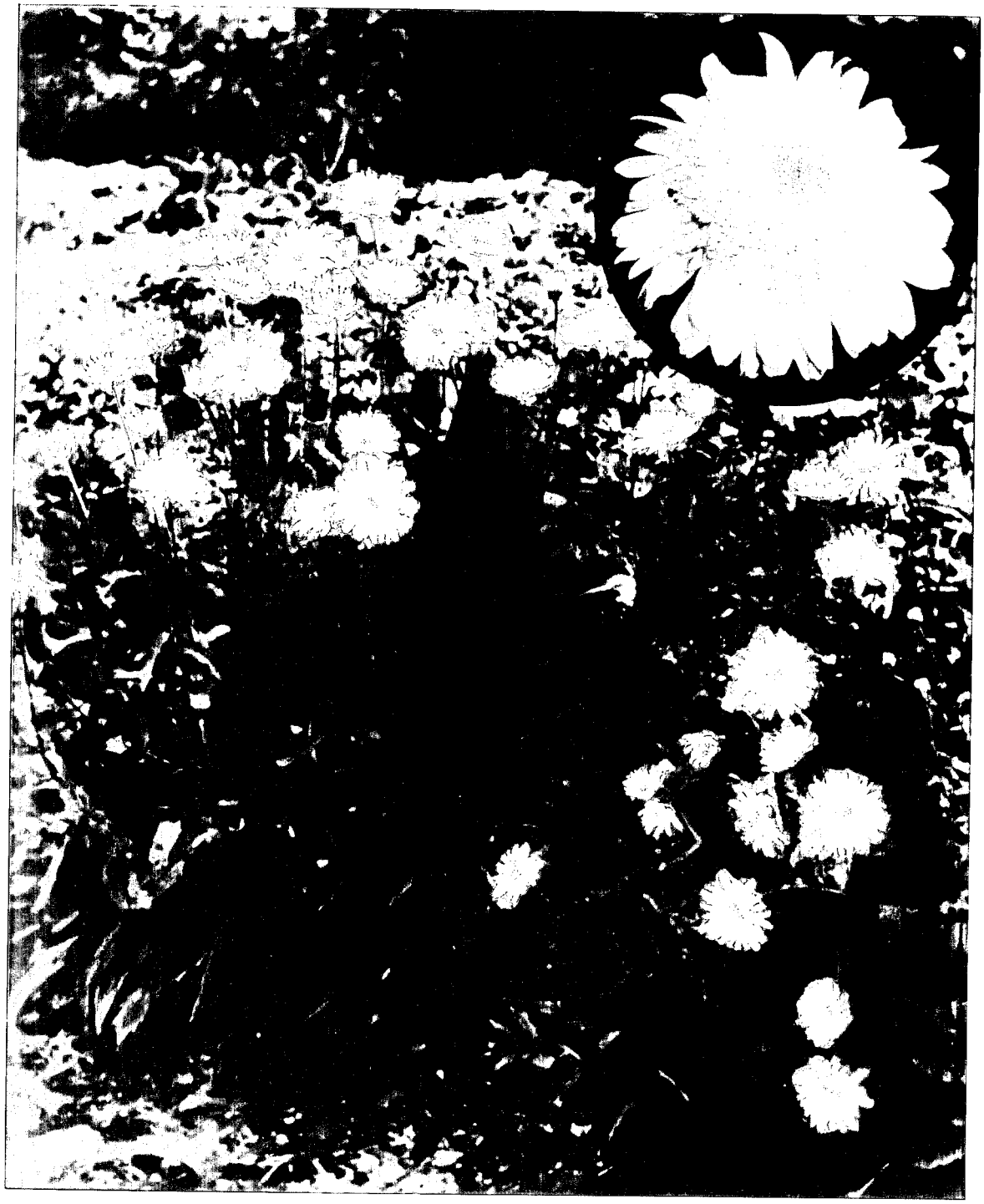
Inventor.
F. G. Read
By: Robert Cobb
Attorneys.

Patented Sept. 2, 1952

Plant Pat. 1,125

UNITED STATES PATENT OFFICE 1,125

SHASTA DAISY PLANT

Francis George Read, Deopham, Wymondham, Norfolk, England, assignor to Jackson & Perkins Company, Newark, N. Y., a corporation of New York Application June 20, 1951, Serial No. 232,515

1 Claim. (Cl. 47—60)

The present invention relates to a new and distinct variety of Shasta daisy plant, originating as a cultivated sport which was discovered by me amongst a cultivated row of plants of "Esther Read," an unpatented variety of *Chrysanthemum maximum*, that were being grown and cultivated by me on my farm at South Cottage, Deopham, Wymondham, Norfolk, England.

My new variety differs distinctly from its parent variety in the following ways, which also distinguish this new variety from all other known varieties of Shasta daisies:

(1) The superior productivity of salable, long-stemmed flowers, exceeding the productive capacity of its parent by 30 to 40 flowers in a single growing season;

(2) The long-lasting quality of the white flowers, both as cut flowers and on the plant, lasting as long as three weeks on the plant and six weeks as cut flowers, which is considerably longer than any other known variety of Shasta daisy is capable of lasting;

(3) The habit of growing much taller than its parent variety;

(4) The habit of blooming later than the parent variety, usually starting to bloom about three weeks later than the parent "Esther Read," but continuing to bloom until frost; and (5) The thick, leathery, and large foliage for a *Chrysanthemum maximum*.

Asexual reproduction of my new variety by root divisions and cuttings in the perennial blocks of a nursery at Newark, New York, shows that the foregoing characteristics come true to form and are established and transmitted through succeeding propagations.

The accompanying drawing illustrates specimens of the new variety, with the blooms in different stages of development from bud to fully open bloom, the inset showing in enlarged detail one of the fully open flowers.

The following is a detailed description of the new variety, reference to color being in accordance with Ridgway's Color Standards and Nomenclature:

Parentage: Sport of *Chrysanthemum maximum* "Esther Read."

Type: Large Anemone-flowered type of *Chrysanthemum maximum*.

Locality where grown and observed: Newark, New York.

Flower:

*Quantity of bloom.*—Very prolific; produces more flowers than "Esther Read." A two-year plant will supply up to 50 flowers with 8 to 10 inch stems.

*Continuity.*—Starts blooming three weeks later than the parent "Esther Read," but continues then until frost.

Bud:

*Form.*—Short; heavy; on stiff stems.

*Color.*—White, Plate 53.

Bloom:

*Type.*—Anemone-flowered type of *Chrysanthemum maximum*.

*Size.*—3½ inches in diameter.

*Form.*—Anemone-type flower. Consists of a large cushion in the center of tubular florets surrounded by 3 rows of ray petals on the outside. These ray petals extend about 1½ inches to 1¾ inches beyond the cushion and they vary in size from ¼ inch to ½ inch in width. The center of the cushion is almost closed except for a very small area of Light Lumiere Green, Plate 17. Cushion—the tubular florets of the cushion begin opening from the outer perimeter and advance toward the center, leaving finally a very small showing of Chalcedony Yellow, Plate 17.

Ray petals:

*Size.*—¼ inch to ½ inch wide.

*Quantity.*—60 petals.

*Color.*—White, Plate 53.

*Lasting quality.*—Flowers last three weeks on plant; 6 weeks as cut flower.

Plant: Stem—36 inches; side branches begin about 8 inches to 10 inches from top.

Foliage:

*Texture.*—Thick, leathery, large foliage for *Chrysanthemum maximum*.

*Length.*—8 inches to 12 inches.

*Quantity.*—Abundant.

*Shape.*—Long; narrow.

*Color.*—Forest Green, Plate 17.

Growth: Strong, spreading root system from which the basal growths are readily made, forming heavy clumps. The root system in contrast with "Esther Read" is completely covered with foliage throughout the season.

I claim:

A new and distinct variety of Shasta daisy plant of the large anemone-flowered type of *Chrysanthemum maximum*, characterized as to novelty by its superior productivity of salable, long-stemmed cut flowers, by the longer-lasting quality of its white flowers both as cut flowers and on the plant, by its thick, leathery, large foliage, and by its taller and later-blooming habits of growth, substantially as herein shown and described.

FRANCIS GEORGE READ.

No references cited.